United States Patent
Neal et al.

(10) Patent No.: US 6,434,418 B1
(45) Date of Patent: Aug. 13, 2002

(54) APPARATUS FOR MEASURING INTRAUTERINE PRESSURE AND FETAL HEART RATE AND METHOD FOR USING SAME

(76) Inventors: Randall H. Neal, 2414 Forbes Dr., Bellevue, NE (US) 68123; Richard C. Neal, 19108 Trailview, San Antonio, TX (US) 78258

( * ) Notice: Subject to any disclaimer, the term of this patent is extended or adjusted under 35 U.S.C. 154(b) by 0 days.

(21) Appl. No.: 09/547,452

(22) Filed: Apr. 12, 2000

(51) Int. Cl.[7] ............................. A61B 5/02; A61B 5/03
(52) U.S. Cl. ......................................... 600/511; 600/376
(58) Field of Search ........................... 600/511, 513, 600/561, 591, 376

(56) References Cited

U.S. PATENT DOCUMENTS

| | | | | |
|---|---|---|---|---|
| 3,326,207 A | * | 6/1967 | Egan | 600/376 |
| 4,063,548 A | * | 12/1977 | Klatt et al. | 600/546 |
| 4,191,196 A | * | 3/1980 | Bradley et al. | 600/546 |
| 4,901,731 A | * | 2/1990 | Millar | 600/488 |
| 5,167,237 A | * | 12/1992 | Rabin et al. | 600/561 |
| 5,425,362 A | * | 6/1995 | Siker et al. | 600/376 |
| 5,433,216 A | * | 7/1995 | Sugrue et al. | 600/591 |
| 5,634,459 A | * | 6/1997 | Gardosi | 600/376 |

* cited by examiner

Primary Examiner—Carl Layno

(57) ABSTRACT

A modified Foley catheter transmits desired data to transducers that allow the measuring of intrauterine pressure and fetal heart rate by healthcare providers on appropriate output devices. A method employs the catheter to indirectly measure intrauterine pressure and fetal heart rate from within the maternal bladder or rectum, thereby allowing the healthcare professional to choose to monitor these fetal characteristics without committing the mother and fetus to childbirth and without the risks associated with intrauterine measuring methods.

10 Claims, 4 Drawing Sheets

APPARATUS FOR MEASURING INTRAUTERINE PRESSURE AND FETAL HEART RATE AND METHOD FOR USING SAME

BACKGROUND OF THE INVENTION

1. Field of the Invention

Applicants' invention relates to a device for measuring intrauterine pressure and fetal heart rate and method for same. More particularly, it relates to a device that employs a Foley-type urinary drainage catheter with a sensing member to measure pressure within the bladder or rectum and correlate the measured pressure to the pressure exerted within the patient's uterus. Additionally, a fetal heart rate sensing member at or near the tip of the catheter is used to measure fetal heart rate from within the maternal bladder or rectum.

2. Background Information

Electronic fetal monitoring is a mainstay of fetal surveillance before and during labor. Much of the analysis focuses on the fetal cardiac responses to various intrinsic and extrinsic provocations, including contractions. Electronic fetal monitoring can predict the absence of asphyxia with greater accuracy than other conventional techniques. Electronic fetal monitoring can improve prenatal outcome by reducing the risk of intrapartum stillbirth and low Apgar scores. It also facilities the physician's ability to diagnose potential abnormalities during labor and allows for early intervention, such as emergency cesarian sections.

Electronic fetal monitoring can employ several modalities. Two of the most common and helpful are measurements of the intrauterine pressure and fetal heart rate. By monitoring the patterns of the fetus' heart rate in time with the intrauterine contractions, the physician can assess possible fetal distress.

Currently, uterine contractile events and fetal heart rate are monitored by external sensors or intrauterine devices. External monitors are safe and noninvasive, but are limited by their inability to assess intrauterine pressure intensity and are hampered by artifacts introduced through sensor placement and abdominal wall thickness. In contrast, internal monitoring provides the physician with more accurate monitoring but requires placement of a monitoring device within the uterus, and on many occasions, placement of a fetal scalp electrode. This type of device requires rupture of the amniotic sac for proper placement. Once the physician determines that internal electronic fetal heart monitoring is advisable, the physician must rupture the sac, irreversibly committing the fetus to delivery. Additionally, the placement and use of an intrauterine device carries risk of placental abruption, chorioamnionitis, fetal laceration, uterine laceration, umbilical cord laceration, and uterine perforation. If a fetal scalp electrode is used, the physician must insert the wire device into the scalp of the fetus which carries risk of fetal bradycardia as well as other risks of infection, bleeding, scarring, and injury.

Even without significant complications, the fetal scalp electrode and the intrauterine pressure catheter partially obstruct the cervical and vaginal canal after placement. The devices may, therefore, interfere with the delivery by their mere presence due to the health provider's hands, instruments, and the baby passing through these same canals.

It would also be advantageous for healthcare providers to be able to monitor the quality of maternal uterine contractions. All muscular activity involves electrical signals that can be detected, including the maternal uterus when contracting during childbirth. An analysis of these signals can provide the healthcare provider with valuable insight regarding the strength, duration, intensity, and change over time of contractions.

Thus, there is a need for a method and device for monitoring intrauterine pressure and fetal heart rate that is more accurate than external devices but safer and less invasive than intrauterine device placement. Further, it is advantageous for the method to avoid placement of the device within the cervical or vaginal canals. Thus, the apparatus must be capable of providing the physician accurate information from a location other than the uterus, cervical canal or vaginal canal. Further, it is advantageous if the device were also capable of measuring the myoelectrical activity of the maternal uterus.

SUMMARY OF THE INVENTION

The present invention incorporates a modified Foley catheter that transmits desired data to transducers allowing monitoring of intrauterine pressure and fetal heart rate by healthcare providers on appropriate output devices. The method of the present invention employs an apparatus to indirectly measure intrauterine pressure and fetal heart rate from within the maternal bladder.

The present invention provides a novel apparatus that will permit the minimally invasive monitoring of a fetus for signs of distress before and during labor. Collected data will provide the physician with improved information to assist in the decision of whether to proceed with more invasive monitoring techniques or emergency procedures, including cesarean sections. Earlier monitoring and intervention may lead to a decrease in the rate of cerebral palsy due to hypoxic injuries sustained during delivery.

The present invention further provides:

a. a novel apparatus for accurately measuring intrauterine pressure, while alleviating the risks associated with conventional, intrauterine devices;

b. a novel apparatus for measuring fetal heart rate as it responds to stimuli, including uterine contractions;

c. a novel apparatus for measuring maternal, uterine myoelectrical signals;

d. a novel apparatus and method to allow the physician to monitor uterine contractions and fetal heart rate from within the maternal bladder without rupturing the amniotic sac and committing the fetus to delivery—allowing the physician to more liberally order such monitoring, not only at the time of delivery, but throughout pregnancy;

e. a novel apparatus and method to allow said measuring with minimal or no obstruction of the cervical and vaginal canals—allowing the physician to work without the interference of wires and/or catheters;

f. a novel method for accurately measuring intrauterine pressures and contractions, including frequency, intensity, and duration of the contractions from the maternal bladder;

g. a novel method for obtaining maternal uterine electromyographic data to better delineate the quality of uterine contractions; and h. a novel method for accurately measuring fetal heart rate simultaneously with measuring uterine pressure and using the same apparatus.

In order to solve the difficulties presented in attempting to obtain these features, a modified Foley catheter and transducer apparatus has been developed which is designed for insertion in the bladder or rectum.

Specifically, the present invention provides for a method and device for indirect monitoring of intrauterine pressure by using direct pressure measurements within the maternal bladder. Simultaneously, the present invention is capable of measuring the heart rate of the intrauterine fetus. Pressure changes within the uterus have corresponding pressure changes in the maternal bladder. Thus, contractions occurring within the uterus are indirectly measurable within the bladder. The present invention employs a modified Foley-type catheter with an integral balloon near the insertion tip that may be filled with fluid. The catheter is inserted in the maternal bladder and the catheter balloon is filled with fluid, securing the insertion tip within the bladder. Urine within the bladder is drained through a drainage port and canal, allowing the tissue surrounding the bladder to collapse snugly against the balloon and insertion tip. In a first embodiment, the fluid filled balloon is in communication with a pressure transducer outside the patient's body via a continuous fluid channel. Thus, as contractions and other pressure changes occur within the uterus and the intraabdominal cavity, they are correspondingly exerted upon the pressure sensing member which indirectly measures intrauterine pressure. If the present invention employs the balloon as the pressure sensing member, pressure exerted in a mechanical fashion on the balloon is transmitted through a communicating, fluid-filled channel to a pressure transducer. An alternative embodiment of the present invention employs an electronic pressure sensor to measure pressure, in which case the resultant electronic signal is communicated along electric leads from the sensing member to the connectors.

The modified Foley catheter has fluid conduits molded into the tube wall material to provide a passage to inflate a balloon near the insertion end for anchoring the catheter in the body. The filled balloon anchors the catheter within the bladder or rectum due to its larger diameter compared to the diameter of the urethra or rectum.

An electrode, or microphone may be inserted or embedded in the catheter near the insertion end to serve as a fetal heart rate sensor. Electrode type sensors are sensitive to the electrical signals produced as the result of muscular activity. Thus, contractions of the fetus' heart produces an electrical signal that is measurable by the electrode type sensor. Alternatively, if an electrode is used, it will also serve to measure maternal, uterine myoelectrical signals. The choice by the healthcare provider to measure fetal heart rate or maternal, uterine myoelectrical signals is a matter of choosing the appropriate signal processing filter to isolate the desired signal. An electronic lead incorporated into the catheter and attached to the heart rate sensor would provide communication to connection end. Alternatively, a Doppler ultrasound probe may be inserted through the catheter utilizing the catheter as a sterile sheath. External transducers and output devices such as monitors or printers, may be connected to the connection end of the catheter and provide for monitoring by the healthcare provider.

The catheter is generally inserted through the urethra into the bladder of the patient, but can be inserted into the rectum as well. Inflation of the balloon anchors the insertion end of the catheter in the bladder and/or rectum. The catheter contains a drainage channel that is open at the insertion end and allows for complete drainage of the bladder.

Pressure changes within the bladder correlate with strong statistical significance to the changes in intrauterine pressures. During pregnancy, contractions and other intrauterine pressure changes are transmitted through the intraabdominal cavity and onto the pressure sensing member of the present invention. When the inflated balloon is being used as the pressure sensor, the fluid channel that allows for inflation of the balloon can be connected to a pressure transducer to measure the mechanical pressure changes on the balloon and convert the pressure changes into numerical measurements that are interpretable by the physician. These pressure measurements correlate with the frequency, strength and length of contractions during labor.

Alternatively, other pressure measuring members may be utilized, such as using a pressure transducer to measure pressure in place of the filled balloon and fluid filled channel. The transducer provides pressure measurements via electrical communication with appropriate output devices. Generally, if a pressure transducer is used, the balloon will be used solely for anchoring purposes. However, should it be desirable, the pressure transducer may be used in combination with the pressure sensing balloon, such that two (2) pressure readings are obtained. The pressure transducer may be located at or near the insertion end of the catheter, or within the balloon itself.

In order to monitor fetal heart sounds and/or rate, an electrode, Doppler ultrasound probe, or microphone apparatus may be implanted or inserted in the catheter wall or lumen at or near the insertion end of the catheter. This places the measuring device or electrode within the maternal bladder, in close proximity to the fetus lying within the uterus. The signal from the fetal heart sensing device may be digitally processed to augment fetal heart signals and/or heart sounds while diminishing or eliminating unwanted signals and sounds such as the maternal electrical signals and/or maternal heart sounds. Alternatively, the signal processing may focus upon maternal myoelectric uterine activity. These signals are then converted into measurable data that is meaningful to the healthcare provider.

The fetal heart monitoring member of the present invention can be configured in a number of ways consistent with the physical requirements of the invention. It may be reusable, and removably insertable in the catheter, or it may be built into the catheter and disposable. The sound sensor may be entirely within the catheter, exposed to catheter environment, or held within a balloon that can be filled with an acoustically enhancing medium.

The method of use of the present invention involves inserting the catheter insertion (distal) end through the mother's urethra into her bladder. The balloon is then inflated, anchoring the insertion tip within the bladder. Generally, urine is then drained from the bladder through the catheter, leaving the balloon and sensors in close contact with the bladder walls. At the connection (proximal) end of the catheter, the fluid filled channel is connected at its outlet end to a pressure transducer. Alternatively, if an internal pressure transducer is being employed, then electronic leads connect the transducer to outside monitoring devices. The fetal heart sensor is likewise connected via electronic leads to outside monitoring devices. Each transducer is attached to a chosen output device, for example a monitor or printer, and the physician is able to monitor the condition of the fetus. Alternatively, the physician would employ the same basic method, however inserting the catheter into the patient's rectum and securing the insertion (distal) end of the catheter at a desired position in the rectum or large intestine. It is possible that both the bladder and rectal methods may be used simultaneously.

DETAILED DESCRIPTION OF THE PREFERRED EMBODIMENT

Figure 1:
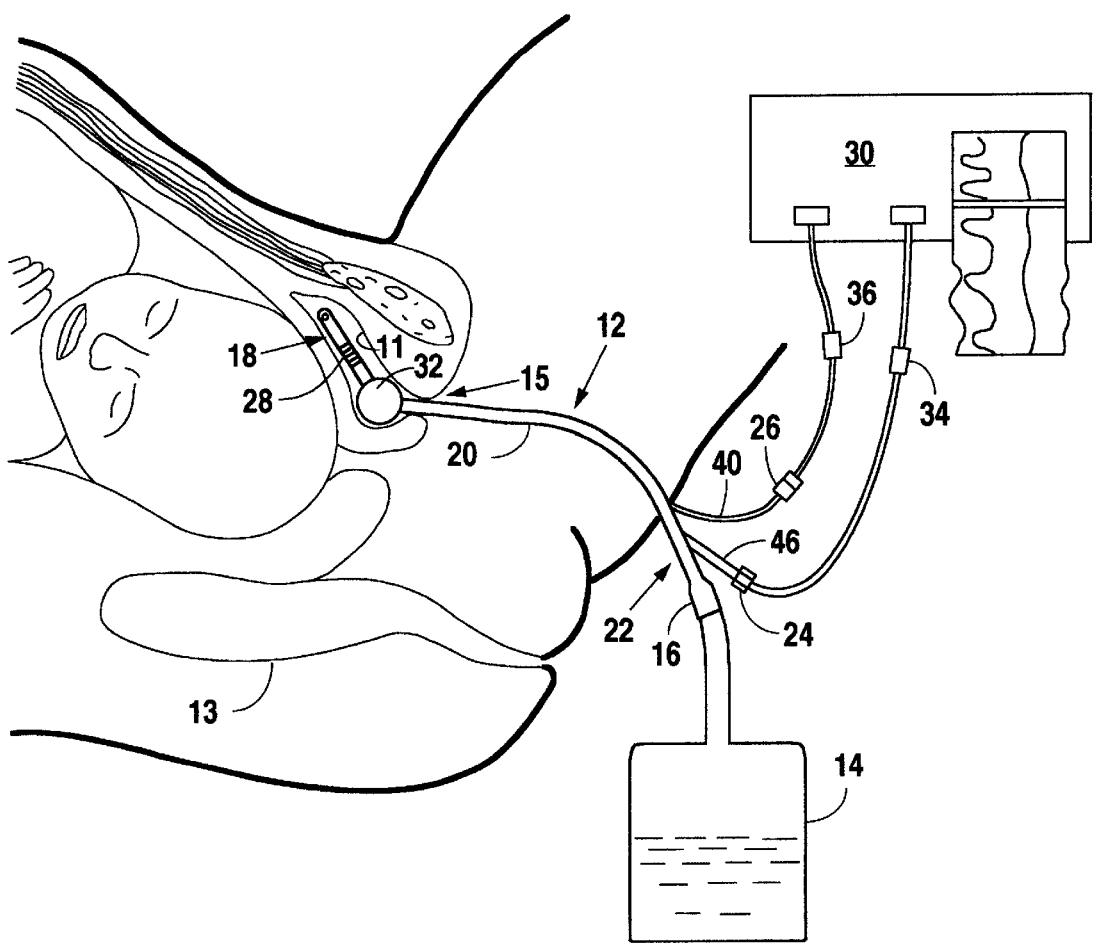
FIG. 1 is a perspective view illustrating placement of the present invention within a bladder to measure intrauterine pressure and/or fetal heart rate during pregnancy or childbirth.

Referring to the figures, FIG. 1, illustrates the manner in which the catheter apparatus (12) of the present invention may be placed in the bladder (11), or rectum (13) of a patient. The catheter (12) is introduced by inserting the insertion end (18) of the catheter (12) through the opening of the maternal urethra (15), urging the flexible tube (20) of the catheter (12) through the urethra (15) into the maternal bladder (11). The insertion end (18) must be sized small enough such that it can move through the urethra (15) into the bladder (11) without damaging the surrounding tissue. Urine from the bladder (11) is drained through a central drainage channel (44) (shown in FIG. 6) in the catheter (12) into a collection reservoir (14) which is removably connected to the catheter (12) at a first connector (16) located at the connection end (22) of the catheter (12). The bladder (11) and rectum (13) are in close proximity to the uterus. Changes in maternal intrauterine pressure correspond directly to changes in pressure within the maternal bladder (11) and rectum (13). The pressure is exerted upon a balloon (32) which is filled with a fluid and is connected to a fluid filled channel (46) running through the flexible tube (20) to a second connector (24). The fluid pressure within the fluid filled channel (46) is measured by a pressure transducer (34) which is connected to an output device (30).

In order to measure fetal heart rate, a fetal heart rate sensor is used to measure the rate of the fetus' heart. In this first embodiment, a fetal heart rate electrode (28) is incorporated at or near the insertion end (18), and may be placed on the balloon (32). Like the pressure, the close proximity of the uterus allows fetal heart rate to be measured from the bladder (11) or rectum (13). The fetal heart rate electrode (28) measures electrical signals generated by the fetus' heart and is attached to a first electronic lead (40) connectable at a third connector (26) and in communication with a fetal heart rate transducer (36), which in turn communicates with an output device (30). There may be more than one fetal heart rate sensor incorporated within the catheter apparatus (12). If the healthcare provider desires to monitor the maternal, uterine myoelectrical signals, then the fetal heart rate electrode (28) could be used in combination with an appropriate signal filter to isolate the uterine signals.

Figure 2:
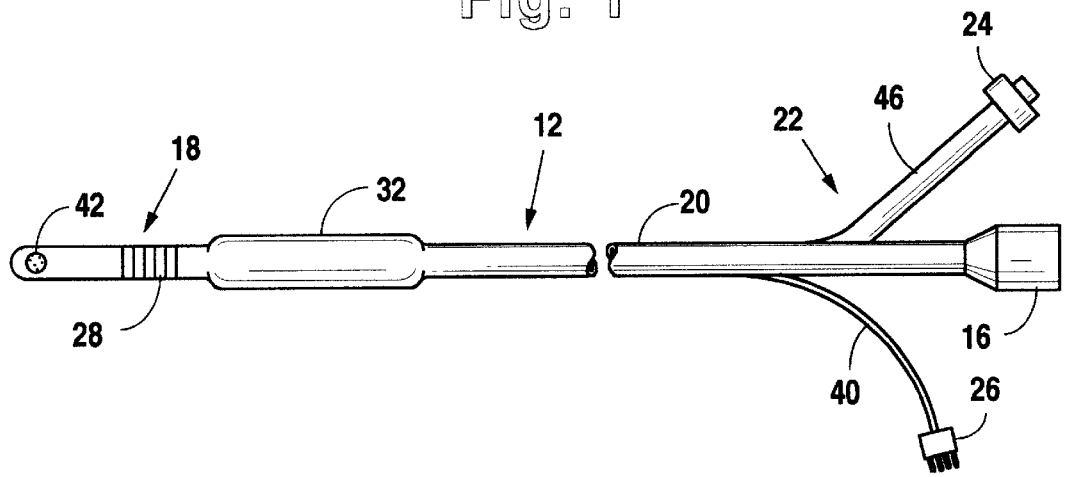
FIG. 2 is a side view of the present invention with the balloon deflated.

FIG. 2 shows the catheter apparatus (12) with the balloon (32) deflated. The insertion end (18) shows the drainage channel opening (42) and fetal heart rate electrode (28). The flexible tube (20) extends to a connection end (22). The balloon (32) is incorporated into the flexible tube (20) and is in communication with a fluid filled channel (46) that extends internally through the flexible tube (20) until it reaches the connection end (22) where it splits away, ending at the second connector (24). The drainage channel opening (42) leads into the drainage channel (44) (shown in FIG. 6) which extends internally through the flexible tube (20) ending at the first connector (16) which provides a means for draining urine from the bladder (11). The fetal heart rate electrode (28) is connected to the third connector (26) by means of a first electronic lead (40) that extends internally through the flexible tube (20).

Figure 3:
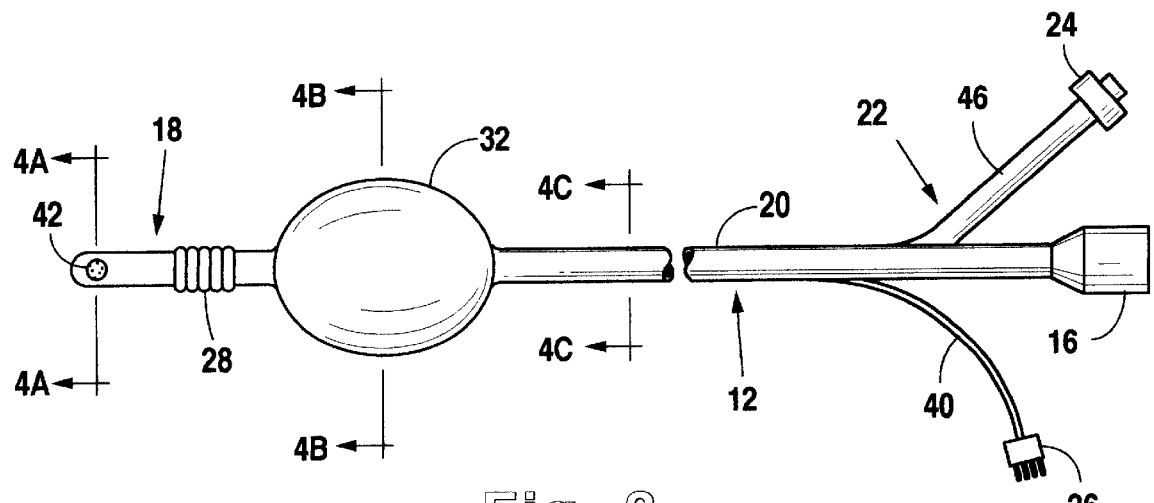
FIG. 3 is a side view of the present invention with the balloon inflated.

FIG. 3 is a side view of the catheter apparatus (12) with the same components as FIG. 2, but showing the balloon (32) inflated.

Figure 4A:
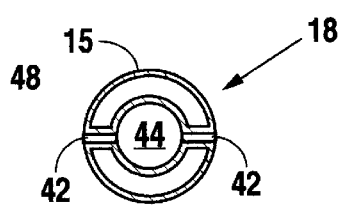
FIG. 4A is a cross sectional view of the present invention taken along line 4A—4A of FIG. 3.

FIG. 4A is a cross sectional view of the catheter apparatus (12) taken along line 4A—4A of FIG. 3. It shows a portion of the insertion end (18) at the point where the drainage channel openings (42) are present to allow urine from the patients bladder (11) to enter the drainage channel (44). The drainage channel (44) is circumscribed by the tube wall (48).

Figure 4B:
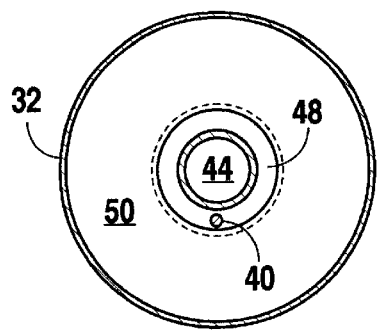
FIG. 4B is a cross sectional view of the present invention taken along line 4B—4B of FIG. 3.

FIG. 4B is a cross sectional view of the catheter apparatus (12) taken along line 4B—4B of FIG. 3. It shows the balloon (32) expanded by fluid (50) away from the tube wall (48). Within the tube wall (48) is the drainage channel (44), and the first electronic lead (40) is shown manufactured into the tube wall (48).

Figure 4C:
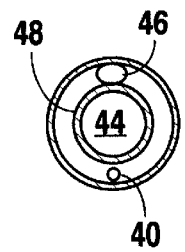
FIG. 4C is a cross sectional view of the present invention taken along line 4C—4C of FIG. 3.

FIG. 4C is a cross sectional view of the catheter apparatus (12) taken along line 4C—4C of FIG. 3. It shows the tube wall (48) surrounding the drainage channel (44) with the first electronic lead (40) and the fluid filled channel (46) manufactured into the tube wall (48).

Figure 5:
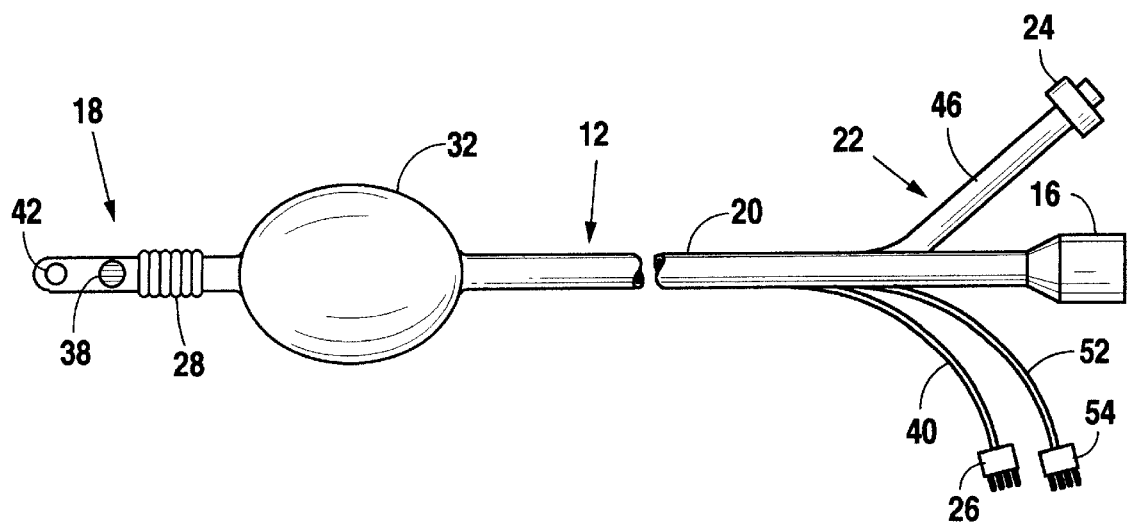
FIG. 5 is a side view of a second embodiment of the present invention incorporating an electronic means for measuring intrauterine pressure.

FIG. 5 is a side view of a second embodiment of the catheter apparatus (12) incorporating an electronic pressure sensor (38) located at or near the insertion end (18) or balloon (32), for measuring intrauterine pressure. While the remainder of the components of the catheter apparatus (12) are the same as FIG. 3, a second electronic lead (52) with a fourth connector (54) are added in order for measurements collected by the electronic pressure sensor (38) to be communicated to a transducer (not shown) and output device (30).

Figure 6:
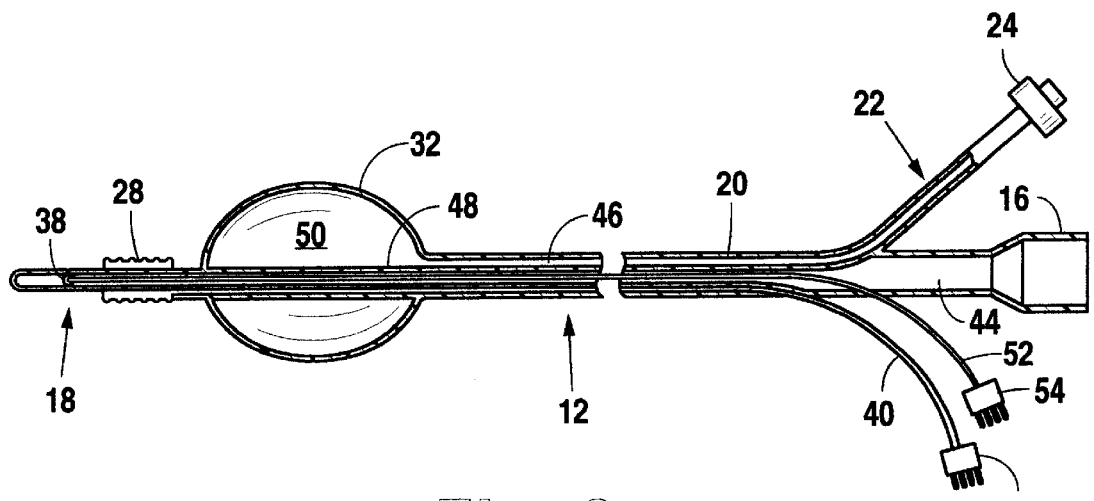
FIG. 6 is a longitudinal transverse section of the embodiment of the present invention as shown in FIG. 5.

FIG. 6 is a longitudinal transverse section of the catheter apparatus (12) shown in FIG. 5. It shows the tube wall (48) extending from the insertion end (18) the length of the catheter apparatus (12) to the connection end (22). The fetal heart rate electrode (28) is attached to the catheter apparatus (12) at or near the insertion end (18) and/or balloon (32). The first electronic lead (40) runs internally through the catheter apparatus (12) from the fetal heart rate electrode (28) to the connection end (22) where the first electronic lead (40) exits the flexible tube (20) and terminates at the third connector (26). The tube wall (48) surrounds the drainage channel (44) which ends at the first connector (16). The balloon (32) is shown expanded and filled with fluid (50).

In order to fill the balloon (32) with fluid (50), the user attaches an inflating device (not shown) to the second connector (24). Fluid (50) is pushed through the fluid filled channel (46), enters and expands the balloon (32). In the first embodiment of the present invention as shown in FIG. 2, the inflating device (not shown) would be disconnected from the second connector (24), and the second connector (24) attached to a pressure transducer (34) in order to measure pressure exerted on the balloon (32). In the second embodiment, as shown in FIG. 6, an electronic pressure sensor (38) is used to measure pressure, and does so by sending an electronic signal along the second electronic lead (52) to the fourth connector (54) which may be attached to a pressure transducer (34).

Figure 7:
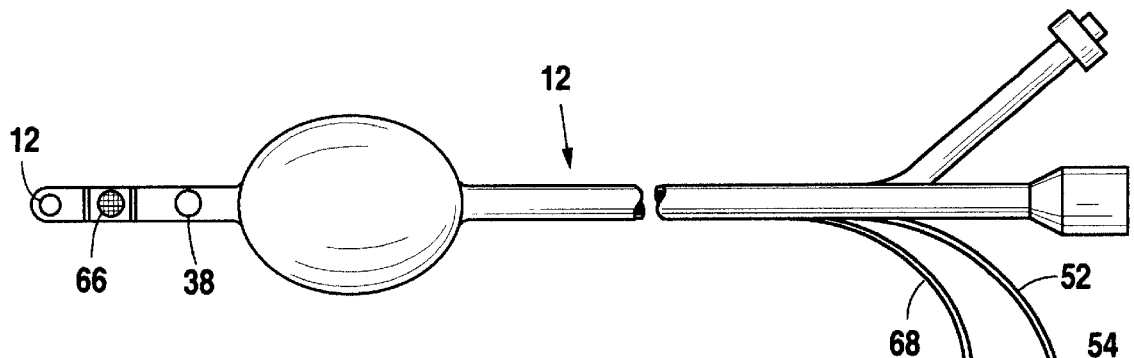
FIG. 7 is a side view of a second embodiment of the present invention incorporating a microphone means for measuring fetal heart rate.

FIG. 7 is a side view of a second embodiment of the catheter apparatus (12) incorporating a microphone (66) for measuring fetal heart rate. This figure illustrates an embodiment in which the fetal heart rate is monitored by a microphone (66) that senses the heart sounds made by the fetal heart beat. A fourth electronic lead (68) connects the microphone (66) to a sixth connector (70), which can be connected to an appropriate transducer (not shown) and output device (30). As in FIG. 6, FIG. 7 illustrates an embodiment in which the intrauterine pressure is measured electronically by the electronic pressure sensor (38) which is in communication with the second electronic lead (52) to the fourth connector (54).

Figure 8:
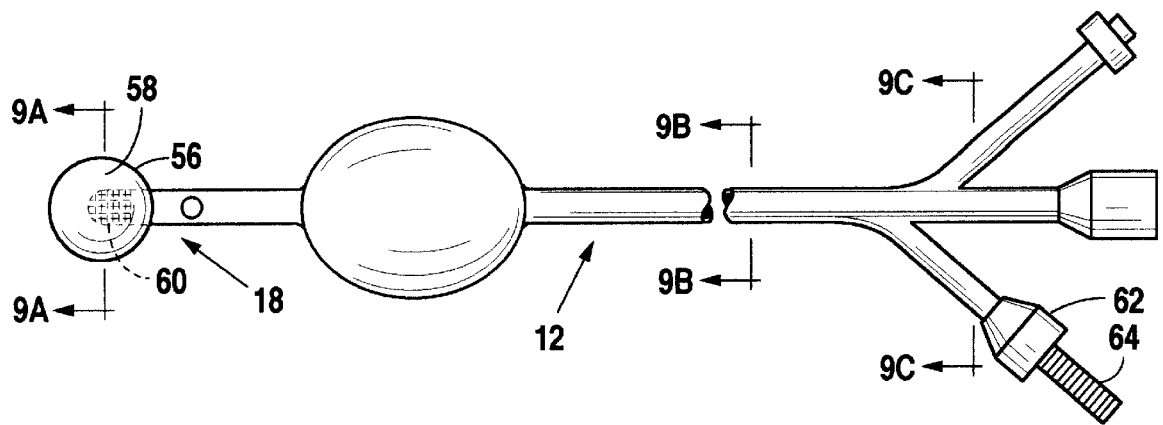
FIG. 8 is a side view of a third embodiment of the present invention incorporating Doppler ultrasound means for measuring fetal heart rate.

FIG. 8 is a side view of a fourth embodiment of the catheter apparatus (12) of FIG. 3, incorporating Doppler ultrasound probe (60) for collecting fetal heart rate in place of the fetal heart rate electrode (28) or microphone (66). A Doppler ultrasound probe (64) is inserted through the catheter apparatus (12) to the insertion end (18). A sheath (56) surrounds the Doppler ultrasound probe tip (60) and is filled with conductive gel (58). The Doppler ultrasound probe (64) extends from the insertion end (18) through the catheter apparatus (12) exits near the connection end (22) and terminates at a fifth connector (62).

Thus, the catheter apparatus (12) provides a sterile sheath for the Doppler ultrasound probe (64).

Figures 9A, 9B, 9C:
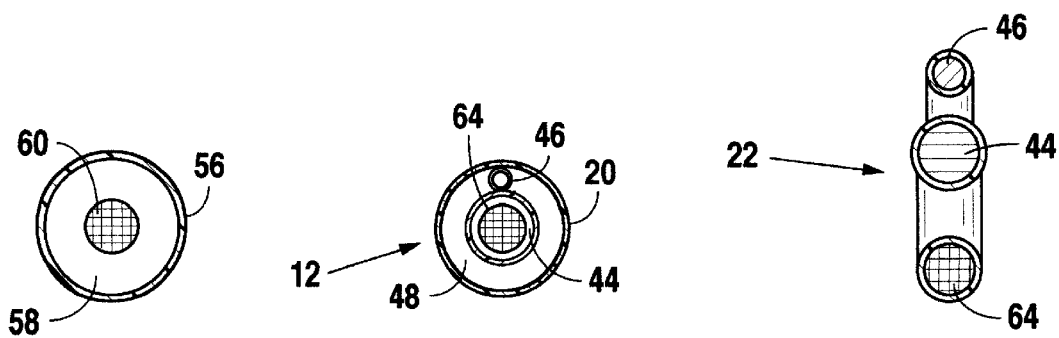
FIG. 9A is a cross sectional view of the present invention taken along line 9A—9A of FIG. 8.
FIG. 9B is a cross sectional view of the present invention taken along line 9B—9B of FIG. 8.
FIG. 9C is a cross sectional view of the present invention taken along line 9C—9C of FIG. 8.

FIG. 9A is a cross sectional view of the present invention taken along line 9A—9A of FIG. 8. It illustrates the position of the Doppler ultrasound probe tip (60) as surrounded by the sheath (56) and the conductive gel (58) filling the space between the sheath (56) and the Doppler ultrasound probe tip (60).

FIG. 9B is a cross sectional view of the present invention taken along line 9B—9B of FIG. 8. It illustrates the orientation of the Doppler ultrasound probe (64) after having been inserted through the length of the catheter apparatus (12) within the flexible tube (20).

The drainage channel (44), fluid filled channel (46), and tube wall (48) are also shown.

FIG. 9C is a cross sectional view of the present invention taken along line 9C—9C of FIG. 8. It illustrates the separation of the Doppler ultrasound probe (64), drainage channel (44), and fluid filled channel (46) at the connection end (22) of the catheter apparatus (12).

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An apparatus for detecting measurements within a human patient comprising:

an elongated flexible tube having an insertion end and a connection end;

an inflatable balloon portion integral to a wall of said flexible tube, near said insertion end;

a channel in said flexible tube having a distal end in communication with said balloon portion and a proximal end substantially adjacent to said connection end of said flexible tube, said proximal end having a connector attachable to either an inflating device or a pressure transducer, and said insertion end and flexible tube sized to be inserted through said human patient's urethra and into said human patient's bladder without causing damage to surrounding tissue;

a pressure transducer connectable to said channel connector, said pressure transducer capable of measuring fluid pressure within said channel.

2. An apparatus for detecting measurements within a human patient comprising:

an elongated flexible tube having an insertion end and a connection end;

an inflatable balloon portion integral to a wall of said flexible tube, near said insertion end;

a channel in said flexible tube having a distal end in communication with said balloon portion and a proximal end substantially adjacent to said connection end of said flexible tube, said proximal end having a connector attachable to either an inflating device or a pressure transducer, and said insertion end and flexible tube sized to be inserted through said human patient's urethra and into said human patient's bladder without causing damage to surrounding tissue;

a fetal heart rate sensor attached to said tube, near said tube insertion end;

a lead connected to said fetal heart rate sensor extending from said fetal heart rate sensor to said tube access end, said lead connectable to a heart rate transducer.

3. The apparatus of claim 2, wherein said fetal heart rate sensor further comprises an electrode.

4. The apparatus of claim 3, wherein said fetal heart rate sensor can detect myoelectric signals from the maternal uterus.

5. The apparatus of claim 2, wherein said fetal heart rate sensor further comprises a microphone.

6. The apparatus of claim 2, wherein said fetal heart rate sensor further comprises a Doppler ultrasound probe.

7. A method for measuring intrauterine pressure of a human patient having an amniotic sac comprising:

inserting a pressure sensor into either the bladder or the rectum of said human patient without rupturing said amniotic sac, said pressure sensor being in communication with a pressure transducer;

securing said pressure sensor within said bladder or rectum, said pressure transducer being in communication with an output device; and activating said pressure sensor to measure intrauterine pressure.

8. The method of claim 7 wherein activating said pressure sensor further comprises:

inflating an inflatable balloon portion integral to a wall of an elongated flexible tube having an insertion end and a connection end, said balloon portion near said insertion end;

determining said intrauterine pressure by reading the pressure applied to said pressure transducer, said pressure transducer attached to a proximal end of a channel in said tube having a distal end in communication with said balloon portion, said proximal end substantially adjacent to said connection end of said flexible tube.

9. A method for measuring heart rate of a fetus within a human patient comprising:

inserting a fetal heart rate sensor into either a bladder or a rectum of a human patient, said heart rate sensor being in communication with a heart rate transducer;

securing said fetal heart rate sensor within said bladder or rectum, said heart rate transducer being in communication with an output device; and activating said fetal heart rate sensor to measure the heart rate of said fetus.

10. The method of claim 9 wherein said heart rate sensor further comprises:

an elongated flexible member having an insertion end and a connection end;

said connection end having a connector attachable to said heart rate transducer;

said insertion end and flexible member sized to be inserted into said bladder or rectum without causing damage to surrounding tissue.

* * * * *

UNITED STATES PATENT AND TRADEMARK OFFICE
CERTIFICATE OF CORRECTION

Page 1 of 1

| | |
|---|---|
| PATENT NO. | : 6,434,418 B1 |
| APPLICATION NO. | : 09/547452 |
| DATED | : August 13, 2002 |
| INVENTOR(S) | : Randall H. Neal & Richard C. Neal |

It is certified that error appears in the above-identified patent and that said Letters Patent is hereby corrected as shown below:

On the Title Page, Item (76) first Inventor requesting that his address, (2414 Forbes Dr., Bellevue, NE 68123) on the Patent be corrected to -- 500 Robin Hood Dr., Yorktown, VA 23693 (US) --.

Signed and Sealed this

Eighteenth Day of September, 2012

David J. Kappos
*Director of the United States Patent and Trademark Office*